United States Patent
Lei et al.

(10) Patent No.: US 8,592,606 B2
(45) Date of Patent: Nov. 26, 2013

(54) LIQUID PRECURSOR FOR DEPOSITING GROUP 4 METAL CONTAINING FILMS

(75) Inventors: Xinjian Lei, Vista, CA (US); John Anthony Thomas Norman, Encinitas, CA (US); Daniel P. Spence, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 328 days.

(21) Appl. No.: 12/950,352

(22) Filed: Nov. 19, 2010

(65) Prior Publication Data
US 2011/0135838 A1 Jun. 9, 2011

Related U.S. Application Data

(60) Provisional application No. 61/267,102, filed on Dec. 7, 2009.

(51) Int. Cl.
C07F 7/00 (2006.01)
C07F 7/28 (2006.01)
C23C 16/00 (2006.01)

(52) U.S. Cl.
USPC ........ 548/402; 427/248.1; 427/535; 427/569; 427/582

(58) Field of Classification Search
USPC ............ 548/402; 427/248.1, 535, 569, 582
See application file for complete search history.

(56) References Cited

U.S. PATENT DOCUMENTS

| 6,552,209 B1 | 4/2003 | Lei et al. |
| 7,560,581 B2 | 7/2009 | Gordon et al. |
| 7,723,535 B2 | 5/2010 | Zhang et al. |
| 2009/0074983 A1 | 3/2009 | Heys et al. |

FOREIGN PATENT DOCUMENTS

| DE | 4120344 | 1/1992 |
| WO | 2007140813 | 12/2007 |
| WO | 2007141059 | 12/2007 |
| WO | 2009/036046 | 3/2009 |
| WO | 2009/036046 A1 | 3/2009 |
| WO | 2009036046 | 3/2009 |
| WO | 2009/155507 A1 | 12/2009 |
| WO | 2009/155520 A1 | 12/2009 |
| WO | 2009155507 | 12/2009 |
| WO | 2009155520 | 12/2009 |

OTHER PUBLICATIONS

Kuhn, N., et al, Xvi *. (2,5-C4tBu2RHN)MCl3 (M=Ti, Zr, Hf; R=H, SiMe3)—Azacyclopentadienyl-Komplexe der Grupee 4-Metalle, Journal of Organometallic Chemistry, 1992, 289-296, 440.

(Continued)

*Primary Examiner* — Porfirio Nazario Gonzalez
(74) *Attorney, Agent, or Firm* — Rosaleen P. Morris-Oskanian; Joseph D. Rossi

(57) ABSTRACT

The present invention is related to a family of liquid group 4 precursors represented by the formula: (pyr*)M(OR$^1$)(OR$^2$)(OR$^3$) wherein pyr* is an alkyl substituted pyrrolyl, wherein M is group 4 metals include Ti, Zr, and Hf; wherein R$^{1-3}$ can be same or different and selected from group consisting of linear or branched C$_{1-6}$ alkyls; preferably C$_{1-3}$ alkyls; R$^4$ is selected from the group consisting of C$_{1-6}$ alkyls, preferably branched C$_{3-5}$ alkyls substituted at 2, 5 positions to prevent the pyrrolyl coordinated to the metal center in η$^1$ fashion; n=2, 3, 4. Most preferably the invention is directed to (2,5-di-tert-butylpyrrolyl)(tris(ethoxy)titanium, (2,5-di-tert-amylpyrrolyl)(tris(ethoxy)titanium, and (2,5-di-tert-amylpyrrolyl)(tris(iso-propoxy)titanium. The invention is also directed to (cyclopentadienyl)(2,5-di-methylpyrrolyl)(bis(ethoxy))titanium. Deposition methods using these compounds are also contemplated.

17 Claims, 5 Drawing Sheets

(56) References Cited

OTHER PUBLICATIONS

Dias, A., et al, Synthesis, characterisation, crystal structure, reactivity and bonding in titanium complexes containing 2,3,4,5-tetramethylpyrrolyl, Journal of the Chemical Society—Dalton Transactions, 1997, 1055-1061.

Black, K., et al, Investigation of New 2,5-Dimethylpyrrolyl Titanium Alkylamide and Alkoxide Complexes as Precursors for the Liquid Injection MOCVD of TiO2, Chem. Vap. Deposition, 2010, 93-99, 16.

Dias, A.R., et al., Synthesis, Characterization and Theoretical Evaluation Of [Ti(NC4Me4)(NMe2)3]—A Complex With N-Bonded 2,3,4,5-Tetramethylpyrrolyl Ligand. Collection of Czechoslovak Chemical Communications, 63(2), pp. 182-186.

LIQUID PRECURSOR FOR DEPOSITING GROUP 4 METAL CONTAINING FILMS

CROSS REFERENCE TO RELATED PATENT APPLICATIONS

The present patent application claims the benefit of U.S. Provisional Patent Application Ser. No. 61/267,102 filed Dec. 7, 2009.

BACKGROUND OF THE INVENTION

This invention is in the field of volatile and liquid Group 4 metal complexes, as precursors for fabricating electronic devices by the semiconductor fabrication industries. Cyclopentadiene based Group 4, as well as other metal complexes, have been intensively explored as potential precursors. Prior art in this field includes:

Kuhn, N., et al., XVI. (2,5-$C_4$t-$Bu_2$RHN)$MCl_3$ (M=Ti, Zr, Hf; R=H, $SiMe_3$)—Azacyclopentadienyl-Komplexe der Gruppe 4-Metalle. Journal of Organometallic Chemistry, 440(3): p. 289-296, 1992.

Dias, A. R., et al., Synthesis, characterisation, crystal structure, reactivity and bonding in titanium complexes containing 2,3,4,5-tetramethylpyrrolyl. Journal of the Chemical Society—Dalton Transactions, p. 1055-1061, 1996.

Dussarrat, C., N. Blasco, A. Pinchart and C. Lachaud "Method of forming high-k dielectric films based on novel titanium, zirconium, and hafnium precursors and their use for semiconductor manufacturing." WO2007140813.

Dussarrat, C., N. Blasco, A. Pinchart and C. Lachaud "Method Of Forming Dielectric Films, New Precursors And Their Use In The Semi-Conductor Manufacturing." WO2007141059A2 (US2009203222A).

Heys, P. N., A. Kingsley, F. Song, P. Williams, T. Leese, H. O. Davies and R. Odedra "Methods Of Atomic Layer Deposition Using Titanium-Based Precursors." US20090074983A1.

Heys, P. N., A. Kingsley, F. Song, P. Williams, T. Leese, H. O. Davies and R. Odedra "Methods Of Preparing Thin Films By Atomic Layer Deposition Using Monocyclopentadienyl Trialkoxy Hafnium And Zirconium Precursors." WO09036046.

Heys, P. N., R. Odedra, A. Kingsley and H. O. Davies, "Titanium Pyrrolyl-Based Organometallic Precursors And Use Thereof For Preparing Dielectric Thin Films", WO09155507 A1.

Heys, P. N., R. Odedra, A. Kingsley and H. O. Davies, "Hafnium And Zirconium Pyrrolyl-Based Organometallic Precursors And Use Thereof For Preparing Dielectric Thin Films", WO09155520 A1.

Black, K., A. C. Jones, J. Bacsa, P. R. Chalker, P. A. Marshall, H. O. Davies, P. N. Heys, P. O'Brien, M. Afzaal, J. Raftery and G. W. Critchlow, "Investigation of new 2,5-dimethylpyrrolyl titanium alkylamide and alkoxide complexes as precursors for the liquid injection mocvd of $TiO_2$." Chemical Vapor Deposition 16(1-3): 93-99 (2010).

BRIEF SUMMARY OF THE INVENTION

The present invention is related to a liquid titanium precursor represented by the formula:

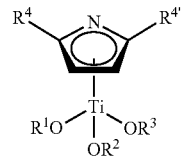

wherein $R^1$, $R^2$ and $R^3$ are the same or different and are selected from the group consisting of ethyl and isopropyl; and $R^4$ and $R^{4'}$ can be same or different and are selected from the group consisting of tert-butyl and tert-amyl, wherein when $R^1$, $R^2$ and $R^3$ are isopropyl, $R^4$ is tert-amyl.

The present invention is also related to Group 4 precursors represented by the formula:

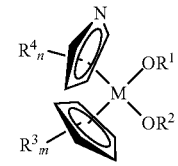

wherein M is a Group 4 metal; wherein $R^{1-2}$ can be same or different and are selected from group consisting of linear or branched $C_{1-6}$ alkyls; $R^3$ can be same or different and are selected from the group consisting of $C_{1-6}$ alkyls, $C_{3-10}$ alkyls containing oxygen or nitrogen atoms, —$CH_2CH_2$OMe and —$CH_2CH_2NMe_2$; m=0, 1, 2, 3, 4, 5; $R^4$ can be same or different organic groups substituted at 2,3,4,5-positions of the pyrrole ring and selected from the group consisting of $C_{1-6}$ alkyls, branched $C_{3-5}$ alkyls substituted at 2, 5 positions, $C_{3-10}$ alkyls containing oxygen or nitrogen atoms, —$CH_2CH_2$OMe and —$CH_2CH_2NMe_2$; n=1, 2, 3, 4; m=0, 1, 2, 3, 4, 5; $R^3$ and $R^4$ can be linked together.

Deposition methods using the two classes of compounds above are also the subject of this invention.

DETAILED DESCRIPTION OF THE INVENTION

Figure 1:
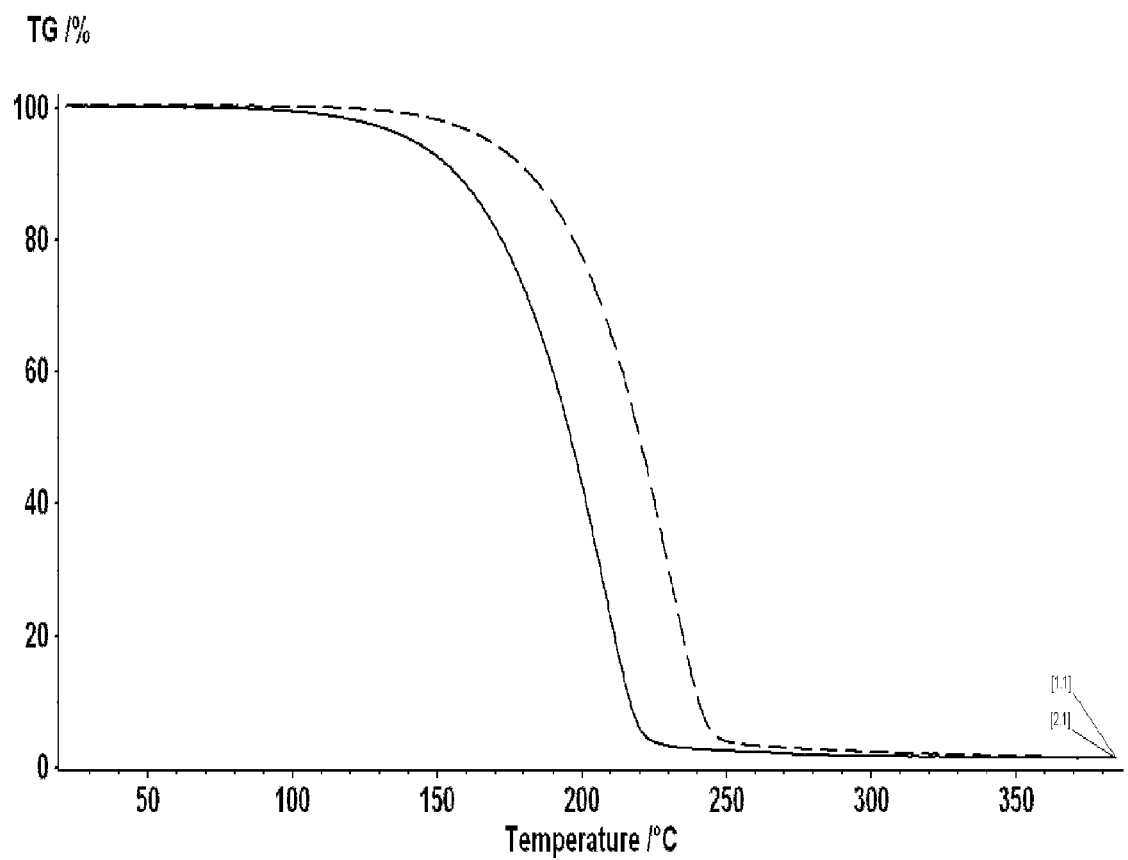
FIG. 1 provides the thermogravometric analysis (TGA) comparison for the evaporation of two Group 4 metal-containing precursors: (2,5-di-tert-butylpyrrolyl)(tris(ethoxy)titanium (represented by the solid line) and (2,5-di-tert-amylpyrrolyl)(tris(ethoxy)titanium (represented by the dashed line), demonstrating that both complexes have smooth and complete vaporization and suggesting that they can be used as potential volatile precursors for CVD or ALD FIG. 2 provides the thermograometric analysis (TGA) comparison of two Group 4 metal-containing precursors: (2,5-di-tert-butylpyrrolyl)(tris(ethoxy)titanium (represented by the solid line) and (2,5-di-tert-butylpyrrolyl)(tris(iso-propoxy)titanium (represented by the dashed line). Both show smooth one-step vaporizations. However the former is more volatile than the latter.

There is a need to develop liquid volatile Group 4 metal complexes as precursors for electronic device fabrication by the semiconductor industries. Cyclopentadiene based Group 4, as well as other metal complexes, have been intensively explored as potential precursors. This invention discloses new species with outstanding properties in a family of liquid Group 4 metal complexes containing both pyrrolyl and alkoxy ligands.

The present invention is related to a family of liquid Group 4 metal precursors represented by the formula: (pyr*)M(OR$^1$)(OR$^2$)(OR$^3$) wherein pyr* is an alkyl substituted pyrrolyl:

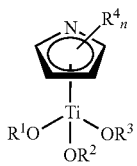

wherein M is Group 4 metals, preferably Ti, Zr, and Hf; wherein R$^{1-3}$ are the same or different and selected from group consisting of linear or branched C$_{1-6}$ alkyls, preferably ethyl or isopropyl groups; R$^4$ can be same or different organic groups substituted at 2,3,4,5-positions of the pyrrole ring and selected from the group consisting of C$_{1-6}$ alkyls, preferably branched C$_{4-5}$ alkyls substituted at 2, 5 positions to prevent the pyrrolyl from coordinating to the metal center in η$^1$ fashion, C$_{3-10}$ alkyls containing oxygen or nitrogen atoms, preferably —CH$_2$CH$_2$OMe and —CH$_2$CH$_2$NMe$_2$; n=2, 3, 4. Exemplary complexes include but not limited:
1. (2,5-di-tert-butylpyrrolyl)(tris(methoxy)titanium
2. (2,5-di-tert-butylpyrrolyl)(tris(ethoxy)titanium
3. (2,5-di-tert-amylpyrrolyl)(tris(methoxy)titanium
4. (2,5-di-tert-amylpyrrolyl)(tris(ethoxy)titanium
5. (2,5-di-tert-amylpyrrolyl)(tris(iso-propoxy)titanium
6. (2,3,5-tri-tert-butylpyrrolyl)(tris(methoxy)titanium
7. (2,3,5-tri-tert-butylpyrrolyl)(tris(ethoxy)titanium
8. (2,3,5-tri-tert-butylpyrrolyl)(tris(iso-propoxy)titanium
9. (2,3,5-tri-tert-amylpyrrolyl)(tris(methoxy)titanium
10. (2,3,5-tri-tert-amylpyrrolyl)(tris(ethoxy)titanium
11. (2,3,5-tri-tert-amylpyrrolyl)(tris(iso-propoxy)titanium
12. (2,3,4,5-tetramethylpyrrolyl)(tris(methoxy)titanium
13. (2,3,4,5-tetramethylpyrrolyl)(tris(ethoxy)titanium
14. (2,3,4,5-tetramethylpyrrolyl)(tris(isoproxy)titanium
15. (2,5-di-tert-amylpyrrolyl)(tris(methoxy)zirconium
16. (2,5-di-tert-amylpyrrolyl)(tris(ethoxy)zirconium
17. (2,5-di-tert-amylpyrrolyl)(tris(iso-propoxy)zirconium
18. (2,3,5-tri-tert-amylpyrrolyl)(tris(methoxy)zirconium
19. (2,3,5-tri-tert-amylpyrrolyl)(tris(ethoxy)zirconium
20. (2,3,5-tri-tert-amylpyrrolyl)(tris(iso-propoxy)zirconium
21. (2,5-di-tert-amylpyrrolyl)(tris(methoxy)hafnium
22. (2,5-di-tert-amylpyrrolyl)(tris(iso-propoxy)hafnium
23. (2,5-di-tert-amylpyrrolyl)(tris(ethoxy)hafnium
24. (tetramethylpyrrolyl)(tris(ethoxy)hafnium
25. (2,3,4,5-tetramethylpyrrolyl)(tris(isoproxy)hafnium The specific preferred embodiments of the present invention are liquid titanium precursors represented by the formula:

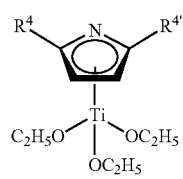

wherein R$^4$ and R$^{4'}$ are the same or different and are selected from the group consisting of tert-butyl and tert-amyl.

Another specific preferred embodiments of the present invention are liquid titanium precursors represented by the formula:

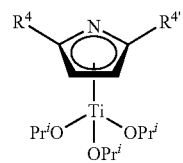

wherein R$^4$ is tert-amyl; R$^{4'}$ is selected from the group consisting of tert-butyl and tert-amyl.

Another family of Group 4 precursors is represented by the formula: (pyr*)(Cp)M(OR$^1$)(OR$^2$), wherein pyr* is an alkyl substituted pyrrolyl and Cp is cyclopentadienyl or alkyl substituted cyclopentadienyl:

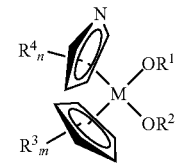

wherein M is Group 4 metals, preferably Ti, Zr, and Hf; wherein R$^{1-2}$ can be same or different and are selected from group consisting of linear or branched C$_{1-6}$ alkyls, preferably C$_{1-3}$ alkyls; R$^3$ can be same or different selected from the group consisting of C$_{1-6}$ alkyls, preferably C$_{1-3}$ alkyls, C$_{3-10}$ alkyls containing oxygen or nitrogen atoms, preferably —CH$_2$CH$_2$OMe and —CH$_2$CH$_2$NMe$_2$; m=0, 1, 2, 3, 4, 5; R$^4$ can be same or different organic groups substituted at 2,3,4,5-positions of the pyrrole ring and is selected from the group consisting of C$_{1-6}$ alkyls, preferably C$_{1-3}$ alkyls, C$_{3-10}$ alkyls containing oxygen or nitrogen atoms, preferably —CH$_2$CH$_2$OMe and —CH$_2$CH$_2$NMe$_2$; n=1, 2, 3, 4; R$^3$ and R$^4$ can also linked together. Examplary complexes include but not limited:

1. (cyclopentadienyl)(2-methylpyrrolyl)(bis(ethoxy)titanium
2. (methylcyclopentadienyl)(2-methylpyrrolyl)(bis(ethoxy)titanium
3. (ethylcyclopentadienyl)(2-methylpyrrolyl)(bis(ethoxy)titanium
4. (propylcyclopentadienyl)(2-methylpyrrolyl)(bis(ethoxy)titanium
5. (cyclopentadienyl)(2-methylpyrrolyl)(bis(methoxy)titanium
6. (methylcyclopentadienyl)(2-methylpyrrolyl)(bis(methoxy)titanium
7. (ethylcyclopentadienyl)(2-methylpyrrolyl)(bis(methoxy)titanium
8. (propylcyclopentadienyl)(2-methylpyrrolyl)(bis(methoxy)titanium
9. (cyclopentadienyl)(2,5-di-methylpyrrolyl)(bis(ethoxy)titanium
10. (cyclopentadienyl)(2,5-di-methylpyrrolyl)(bis(methoxy)titanium
11. (methylcyclopentadienyl)(2,5-di-methylpyrrolyl)(bis(methoxy)titanium
12. (ethylcyclopentadienyl)(2,5-di-methylpyrrolyl)(bis(methoxy)titanium
13. (propylcyclopentadienyl)(2,5-di-methylpyrrolyl)(bis(methoxy)titanium
14. (methylcyclopentadienyl)(2,5-di-methylpyrrolyl)(bis(ethoxy)titanium
15. (ethylcyclopentadienyl)(2,5-di-methylpyrrolyl)(bis(ethoxy)titanium
16. (propylcyclopentadienyl)(2,5-di-methylpyrrolyl)(bis(ethoxy)titanium Disclosed herein are precursors for depositing Group 4 metal-containing films. Also disclosed herein are methods for making the precursors, along with methods for depositing the Group 4 metal-containing films. With regard to the later, the method described herein is a method for forming a metal-containing film, such as, but not limited to, strontium titanate and barium strontium titanate, titanium doped lanthanide oxide, titanium doped zirconium, titanium doped hafnium oxide using deposition processes, such as, but not limited to, atomic layer deposition (ALD) or cyclic chemical vapor deposition (CCVD) that may be used, for example, as a gate dielectric or capacitor dielectric film in a semiconductor device.

With each generation of metal oxide semiconductor (MOS) integrated circuit (IC), the device dimensions have been continuously scaled down to provide for high-density and high-performance, such as high speed and low power consumption requirements. Unfortunately, field effect semiconductor devices produce an output signal that is proportional to the width of the channel, such that scaling reduces their output. This effect has generally been compensated for by decreasing the thickness of gate dielectric, thus bring the gate in closer proximity to the channel and enhancing the field effect, which thereby increases the drive current. Therefore, it has become increasingly important to provide extremely thin reliable and low-defect gate dielectrics for improving device performance.

In addition to minimizing side reactions with the substrate that the Group 4 precursor is deposited upon, it is also desirable that the Group 4 precursor is thermally stable, and preferably in liquid form. Group 4-containing metal films are typically deposited using a vapor deposition (e.g., chemical vapor deposition and/or atomic layer deposition) process. It is desirable that these precursors are thermally stable during vapor delivery in order to avoid premature decomposition of the precursor, before it reaches the vapor deposition chamber during processing.

Also described herein is a method for making a Group 4 metal-containing oxide film, metal-containing nitride film, metal-containing oxynitride film, metal-containing silicate film, multi-component metal oxide film, and any combination or laminate thereof, which may be used, for example, in fabricating semiconductor devices. In one embodiment, the method disclosed herein provides a Group 4 metal or multi-component metal oxide film that has a dielectric constant substantially higher than that of either conventional thermal silicon oxide, silicon nitride, or zirconium/hafnium oxide dielectric.

The method disclosed herein deposits the Group 4 metal containing films using atomic layer deposition (ALD) or chemical vapor deposition (CVD) processes, preferably an ALD process. Examples of suitable deposition processes for the method disclosed herein include, but are not limited to, cyclic chemical vapor deposition (CCVD), MOCVD metal organic chemical vapor deposition (MOCVD), thermal chemical vapor deposition, plasma enhanced chemical vapor deposition (PECVD), photon assisted chemical vapor deposition (PACVD), plasma-photon assisted chemical vapor deposition (PPECVD), cryogenic chemical vapor deposition, chemical assisted vapor deposition, and hot-filament chemical vapor deposition. In certain embodiments, the metal containing films are deposited via thermal ALD or plasma enhanced cyclic ALD (PEALD) process. In these embodiments, the deposition temperature may be relatively lower, preferably a range from 200° C. to 500° C., and may allow for a wider process window to control the specifications of film properties required in end-use applications. Exemplary deposition temperatures for the ALD or CCVD deposition include ranges having any one or more of the following endpoints: 200, 225, 250, 275, 300, 325, 350, 375, and/or 400° C.

In certain embodiments, other metal-containing precursors can be used in addition to the Group 4 metal-containing precursors described herein. Metals commonly used in semiconductor fabrication, include those that can be used as the metal component such as: titanium, tantalum, tungsten, hafnium, zirconium, cerium, zinc, thorium, bismuth, lanthanum, strontium, barium, lead, and combinations thereof.

Examples of other metal-containing precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino)hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino)bis(ethylmethylamino)tungsten, bis(2,2,6,6-tetramethyl-3,5-heptanedionato)strontium, bis(2,2,6,6-tetramethyl-3,5-heptanedionato)barium, tris(2,2,6,6-tetramethyl-3,5- heptanedionato)lanthanides; $M(R_mC_{5-m-n}H_n)_2$ wherein M=Sr or Ba, n is a integer from 1 to 4, n+m=5; $M(R_mC_{5-m-n}H_n)_3$ wherein M=lanthanide elements such as La, Pr, Nd, Gd, Er, Yb, Lu, n is a integer from 1 to 4, n+m=5; and combinations thereof.

In one embodiment of the method described herein, a cyclic deposition process such as CCVD, ALD, or PEALD may be employed, wherein a Group 4 metal-containing precursor or its solution and an oxygen source such as, for example, ozone, oxygen plasma or water plasma are employed. The gas lines connecting from the precursor canisters to the reaction chamber are heated to one or more temperatures ranging from about 100° C. to about 200° C. depending upon the process requirements, and the container of the Group 4 metal-containing precursor is kept at one or more temperatures ranging from about 100° C. to about 190° C. for dispensing, wherein the solution comprising the Group 4 metal-containing precursor is injected into a vaporizer kept at one or more temperatures ranging from about 150° C. to about 200° C. for direct liquid injection. A flow of 100-2000 sccm of inert gas such as argon or nitrogen may be employed as a carrier gas to help deliver the vapor of the Group 4 metal-containing precursor to the reaction chamber during the precursor pulsing. The reaction chamber process pressure is in the range of 0.1 to 10 Torr.

In a typical ALD or CCVD process, the substrate, such as silicon oxide or metal nitride, are heated on a heater stage in a reaction chamber that is exposed to the Group 4 metal-containing precursor initially to allow the complex to chemically adsorb onto the surface of the substrate. An inert gas, such as argon, purges away unadsorbed excess complex from the process chamber. After sufficient Ar purging, an oxygen source is introduced into reaction chamber to react with the absorbed surface followed by another inert gas purge to remove reaction by-products from the chamber. The process cycle can be repeated to achieve the desired film thickness.

In liquid delivery formulations, the precursors described herein may be delivered in neat liquid form, or alternatively, may be dissolved in a suitable solvent or mixture of solvents and the resulting solution vaporized for us by DLI. Thus, in certain embodiments the precursor formulations may include solvent component(s) of suitable character, as may be desirable and advantageous in a given end use application to form a film on a substrate.

The solvent employed in solubilizing the precursor for use in a deposition process may comprise of any compatible solvent or mixtures of solvent, including; aliphatic hydrocarbons (e.g., pentane, hexane, heptane, octane, decane, dodecane, ethylcyclohexane, propylcyclohexane), aromatic hydrocarbons (e.g., benzene, toluene, ethylbenzene, xylene, mesitylene, ethyl toluene and other alkyl substituted aromatic solvents), ethers, esters, nitriles, alcohols, amines (e.g., triethylamine, tert-butylamine), imines and carbodiimides (e.g., N,N'-diisopropylcarbodiimide), ketones, aldehydes, amidines, guanadines, isoureas, and the like.

Further examples of suitable solvents are selected from the group consisting of glyme solvents having from 1 to 6 oxygen atoms (e.g. dimethoxyethane, 1,2-diethoxyethane, diglyme and triglyme); organic ethers selected from the group consisting of propylene glycol groups (e.g. dipropylene glycol dimethyl ether); $C_2$-$C_{12}$ alkanols; organic ethers selected from the group consisting of dialkyl ethers comprising $C_1$-$C_6$ alkyl moieties, $C_4$-$C_8$ cyclic ethers (e.g. tetrahydrofuran and dioxane); $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines, aminoethers and organic amides.

The utility of specific solvent compositions for particular precursors may be readily empirically determined, to select an appropriate single component or multiple component solvent medium for the liquid delivery vaporization and transport of the specific Group 4 metal precursor that is employed.

In another embodiment, a direct liquid delivery method can be employed by dissolving the Group 4 metal-containing precursor in a suitable solvent or a solvent mixture to prepare a solution with a molar concentration from 0.01 to 2 M, depending the solvent or mixed-solvents employed. The solvent employed herein may comprise any compatible solvents or their mixture including, but not limited to, aliphatic hydrocarbons, aromatic hydrocarbons, linear or cyclic ethers, esters, nitriles, alcohols, amines, polyamines, aminoethers and organic amides, preferably a solvent with a high boiling point, such as octane, ethylcyclohexane, decane, dodecane, xylene, mesitylene and dipropylene glycol dimethyl ether.

In one particular embodiment, the resultant metal oxide films can be exposed to a post-deposition treatment, such as a thermal or plasma treatment to densify the film at temperature below 600° C.

As mentioned previously, the method described herein may be used to deposit a metal-containing film on at least a portion of a substrate. Examples of suitable substrates include, but are not limited to, semiconductor materials, such as strontium titanate, barium strontium titanate, yttrium oxide doped with titanium, lanthanum oxide doped with titanium, and other lanthanide oxides doped with titanium.

The following examples illustrate the method for preparing a Group 4 metal-containing precursor described herein are not intended to limit it in any way.

EXAMPLE 1

Synthesis of (2,5-di-tert-butylpyrrolyl)(tris(ethoxy)titanium

To a white suspension of 4.24 g (22.88 mmol) 2,5-di-tert-butylpyrrolyl lithium salt in 50 mL of hexanes at room temperature was added 5.0 g (22.88 mmol) of TiCl (EtO)$_3$ in 25 mL of hexanes. The white suspension became a mud like color and consistency upon addition of the TiCl (EtO)$_3$. The reaction mixture was refluxed for several hours, after which the suspension was filtered. The filtrate was pumped under vacuum to provide 7.53 g of a brown-red liquid. Vacuum distillation at 100° C. under 200 mTorr provided 5.9 g of yellow amber slightly viscous liquid. The yield was 71%.

$^1$H-NMR (500 MHz, C$_6$D$_6$) δ(ppm): 6.39 (s, 2H), 4.34 (q, 6H), 1.51 (s, 18H), 1.16 (t, 9H).

EXAMPLE 2

Synthesis of (2,5-di-tert-amylpyrrolyl)(tris(ethoxy)titanium

To a white suspension of 9.91 g (46.45 mmol) 2,5-di-tert-amyl pyrrolyl lithium salt in 100 mL of hexanes at room temperature was added 10.15 g (46.45 mmol) of TiCl(EtO)$_3$ in 50 mL of hexanes. The white suspension became an olive green color upon addition of the TiCl(EtO)$_3$. The reaction mixture was refluxed for 16 hours, after which the suspension was filtered. The filtrate was pumped under vacuum to provide 17.49 g of an olive green liquid. The crude yield was 97%.

$^1$H-NMR (500 MHz, C$_6$D$_6$) δ(ppm): 6.39 (s, 2H), 4.36 (q, 6H), 1.71 (q, 4H), 1.52 (s, 12H), 1.16 (t, 9H), 0.79 (t, 6H).

FIG. 1 provides the thermogravometric analysis (TGA) comparison for the evaporation of two Group 4 metal-containing precursors: (2,5-di-tert-butyl)pyrrolyl)(tris(ethoxy) titanium (represented by the solid line) and (2,5-di-tert-amyl) pyrrolyl)(tris(ethoxy)titanium (represented by the dashed line). FIG. 1 shows that the two precursors, or the Group 4 metal-containing precursors described herein, are volatile and leave almost no residue, indicating they can be good precursors for depositing Ti-containing films by CVD, ALD or similar metal vapor based film growth techniques.

COMPARATIVE EXAMPLE 3

Synthesis of (2,5-di-tert-butylpyrrolyl)(tris(iso-propoxy))titanium

To a white suspension of 3.55 g (19.19 mmol) 2,5-di-tert-butylpyrrolyl lithium salt in 40 mL of hexanes at room temperature was added 5.00 g (19.19 mmol) of TiCl(OPr$^i$)$_3$ in 10 mL of hexanes. The white suspension became a mud like color upon addition of the TiCl(OPr$^i$)$_3$. Refluxed reaction mixture for 16 hours after which the suspension was filtered. The filtrate was pumped under vacuum to provide a dark brown liquid. The crude material was subjected to vacuum distillation heating at 130° C. under 200 mTorr vacuum. Transferred over 4.41 g of an amber colored liquid. The yield was 57%.

$^1$H-NMR (500 MHz, C$_6$D$_6$) δ(ppm): 6.37 (s, 2H), 4.64 (m, 3H), 1.54 (s, 18H), 1.20 (d, 18H).

Figure 2:
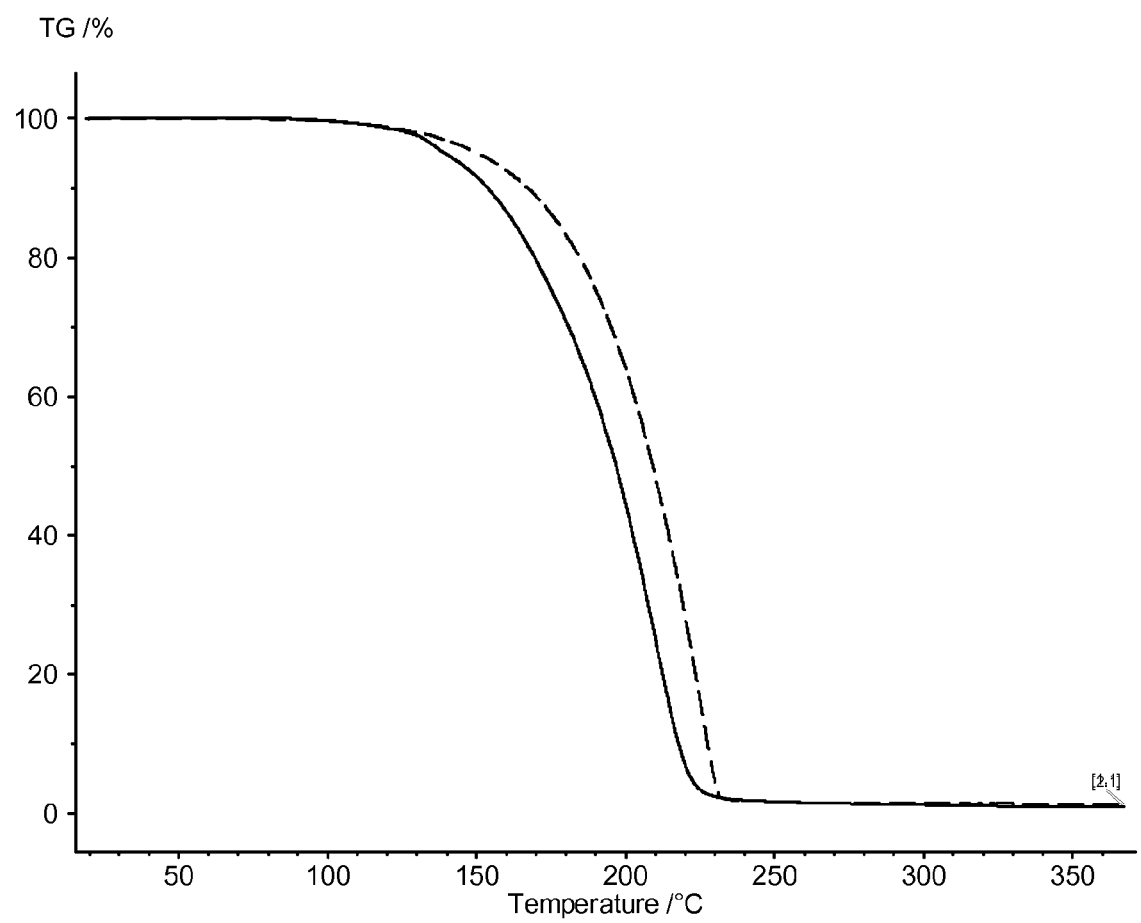

FIG. 2 provides the thermograometric analysis (TGA) curves and their corresponding first derivative (DTG) comparison of two Group 4 metal-containing precursors: (2,5-di-tert-butylpyrrolyl)(tris(ethoxy)titanium (represented by the solid line) and (2,5-di-tert-butylpyrrolyl)(tris(iso-propoxy)titanium (represented by the dashed line). both show smooth one-step vaporization, however (2,5-di-tert-butylpyrrolyl) (tris(ethoxy)titanium is more volatile than (2,5-di-tert-butylpyrrolyl)(tris(iso-propoxy)titanium.

COMPARATIVE EXAMPLE 4

Synthesis of (2,5-di-methylpyrrolyl)(tris(ethoxy)titanium dimer

To a solution of 2.0 g (9.15 mmol) of chlorotris(ethoxy) titanium in 30 mL of THF at −40° C. was added 0.93 g (9.15 mmol) of 2,5-dimethylpyrrolyl lithium salt as a suspension in 20 mL of THF. The resulting reaction mixture turned a dark red-brown. The reaction was stirred for 16 hours after which volatiles were removed under vacuum to afford a burgundy colored solid that was extracted with 75 mL of hexanes. Filtration and removal of hexanes yielded 2.40 g of a red brown solid with a yield of 94%.

$^1$H-NMR (500 MHz, C$_6$D$_6$) δ(ppm): 6.06, 5.89 (two s, 2H, pyr*), 4.20, 4.02 (two quartets, 6H, OCH$_2$CH$_3$), 2.56, 2.42 (two s, 6H, CH$_3$ of pyr*), 1.05, 0.93 (two triplets, 9H, OCH$_2$CH$_3$).

X-ray diffraction of a crystal grown in hexane solution showed it is a dimer, in which two titanium atoms are bridged by two ethoxy groups. Each titanium is also coordinated to an additional two ethoxy groups and one 2,5-dimethylpyrrolyl via η$^1$ fashion. The structure is similar to (2,5-di-methylpyrrolyl)(tris(iso-propoxy)titanium dimer reported by Black, K., A. C. Jones, J. Bacsa, P. R. Chalker, P. A. Marshall, H. O. Davies, P. N. Heys, P. O'Brien, M. Afzaal, J. Raftery and G. W. Critchlow (2010). "Investigation of new 2,5-dimethylpyrrolyl titanium alkylamide and alkoxide complexes as precursors for the liquid injection mocvd of TiO$_2$", Chemical Vapor Deposition 16(1-3): 93-99 (2010).

Figure 3:
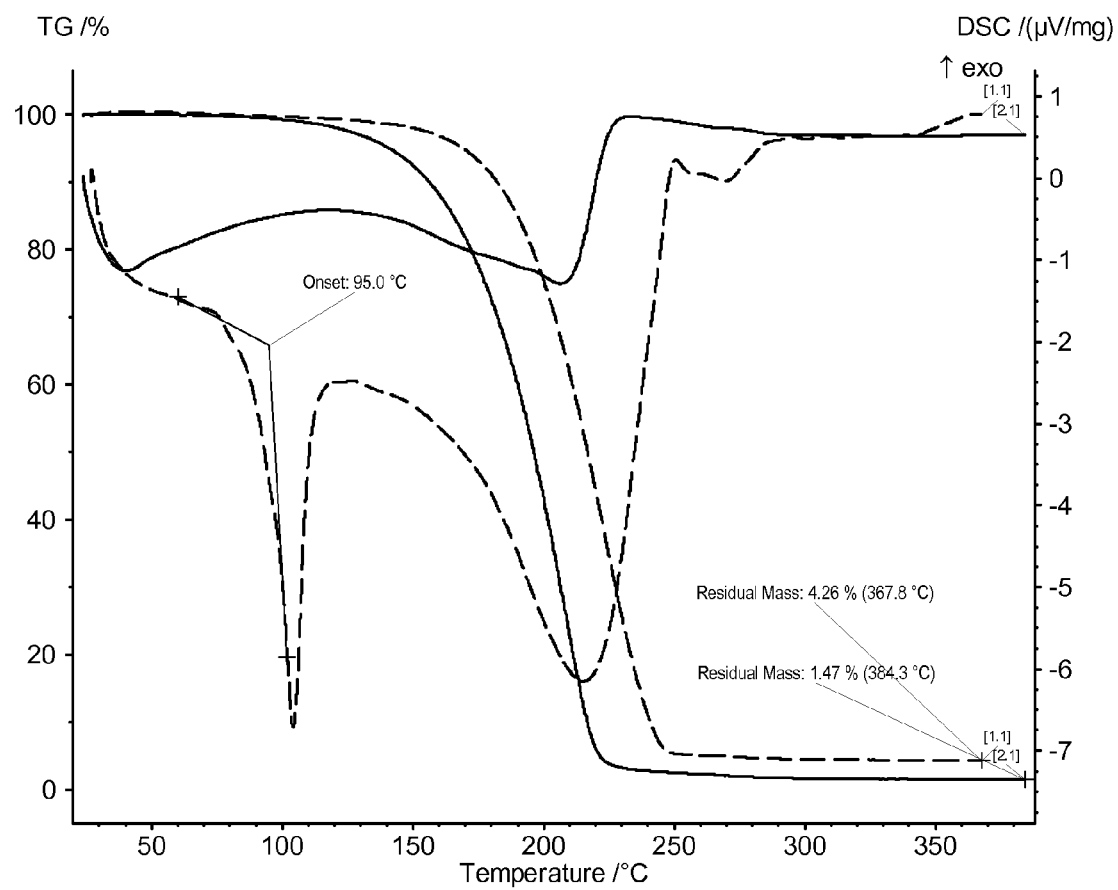
FIG. 3 provides the thermogravometric analysis (TGA) and differential scanning calorimetry (DSC) comparison of two Group 4 metal-containing precursors: (2,5-di-tert-butylpyrrolyl)(tris(ethoxy)titanium (represented by the solid line) and (2,5-di-methylpyrrolyl)(tris(ethoxy)titanium dimer (represented by the dashed line). Both show smooth vaporization, however (2,5-di-tert-butylpyrrolyl)(tris(ethoxy)titanium is a liquid at room temperature and more volatile, whereas (2,5-di-methylpyrrolyl)(tris(ethoxy)titanium is a solid with melting point of 95° C., as shown in the DSC curve and less volatile, indicating that (2,5-di-tert-butylpyrrolyl)(tris(ethoxy)titanium is a superior precursor for CVD/ALD than (2,5-di-methylpyrrolyl)(tris(ethoxy)titanium dimer.

The melting point of (2,5-di-methylpyrrolyl)(tris(ethoxy) titanium dimer is measured by DSC as 95° C. FIG. 3 provides TGA and DSC comparison of (2,5-di-tert-butylpyrrolyl)(tris (ethoxy)titanium (represented by the solid line) vs (2,5-di-methylpyrrolyl)(tris(ethoxy)titanium dimer (represented by the dashed line). Both seem to have smooth vaporization, however (2,5-di-tert-butylpyrrolyl)(tris(ethoxy)titanium is a liquid at room temperature and more volatile, whereas (2,5-di-methylpyrrolyl)(tris(ethoxy)titanium dimer is a solid and less volatile, indicating (2,5-di-tert-butylpyrrolyl)(tris (ethoxy)titanium would be more desirable as a CVD/ALD precursor than (2,5-di-methylpyrrolyl)(tris(ethoxy)titanium dimer.

EXAMPLE 5

Synthesis of (cyclopentadienyl)(2,5-di-methylpyrrolyl)(bis(ethoxy)titanium

To a solution of 1.0 g (3.60 mmol) bis(chloro)(2,5-dimethylpyrrolyl)(cyclopentanyl)titanium in 30 mL of toluene was added 0.37 g (7.19 mmol) lithium ethoxide directly. The reaction was refluxed for an extent of 16 hours after which removal of volatiles and extraction with hexane afforded a red-brown waxy solid weighing 0.94 g. Additionally, the insoluble solid of the hexanes extract was within the amount predicted for LiCl. Sublimation was carried out for the crude material by heating at 110° C. under 0.20 torr vacuum for an extent of 16 hours. A minimal amount of a clumpy red-orange solid was recovered from the sublimer's cold finger. The oily residual left at the bottom of sublimer became a crystalline solid after it cooled. The crude yield was 88%. The melting point of (cyclopentadienyl)(2,5-di-methylpyrrolyl)(bis (ethoxy)titanium is measured by DSC as 78° C.

$^1$H-NMR (500 MHz, C$_6$D$_6$) δ(ppm): 6.21 (s, 2H, pyr*), 5.93 (s, 5H, Cp), 4.09 (q, 4H, OCH$_2$CH$_3$), 2.28 (s, 6H, CH$_3$ of pyr*), 0.96 (t, 6H, OCH$_2$CH$_3$).

Figure 4:
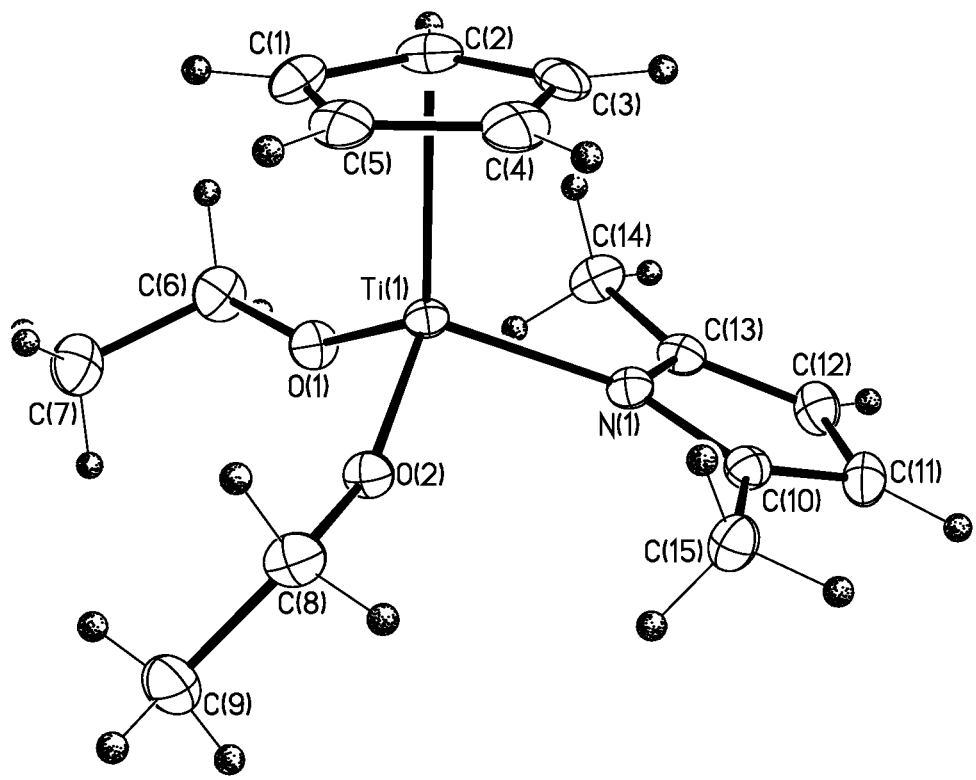
FIG. 4 is a schematic representation of the crystal structure of (cyclopentadienyl)(2,5-di-methylpyrrolyl)(bis(ethoxy)titanium.

FIG. 4 is the crystal structure, showing the cyclopentadienyl group coordinated in η$^5$ fashion to the titanium atom whereas the 2,5-dimethylpyrrolyl coordinated in η1 coordination mode.

EXAMPLE 6

ALD of TiO$_2$ using (2,5-di-tert-butylpyrrolyl)(tris(ethoxy) titanium

This example describes an ALD of TiO$_2$ using (2,5-di-tert-butylpyrrolyl)(tris(ethoxy)titanium and ozone. The deposition temperature range is 200~400° C. The deposition chamber pressure is around 1.5 Torr. The container for (2,5-di-tert-butylpyrrolyl)(tris(ethoxy)titanium was kept at 100° C. One cycle of ALD or CCVD of TiO$_2$ consists of 4 steps.

1. Introduce titanium precursor via bubbling with Ar as carrier gas;
2. Ar purge to remove away any left over titanium precursor with Ar;
3. Introduce ozone into the deposition chamber, and;
4. Ar purge to remove away any unreacted ozone.

Figure 5:
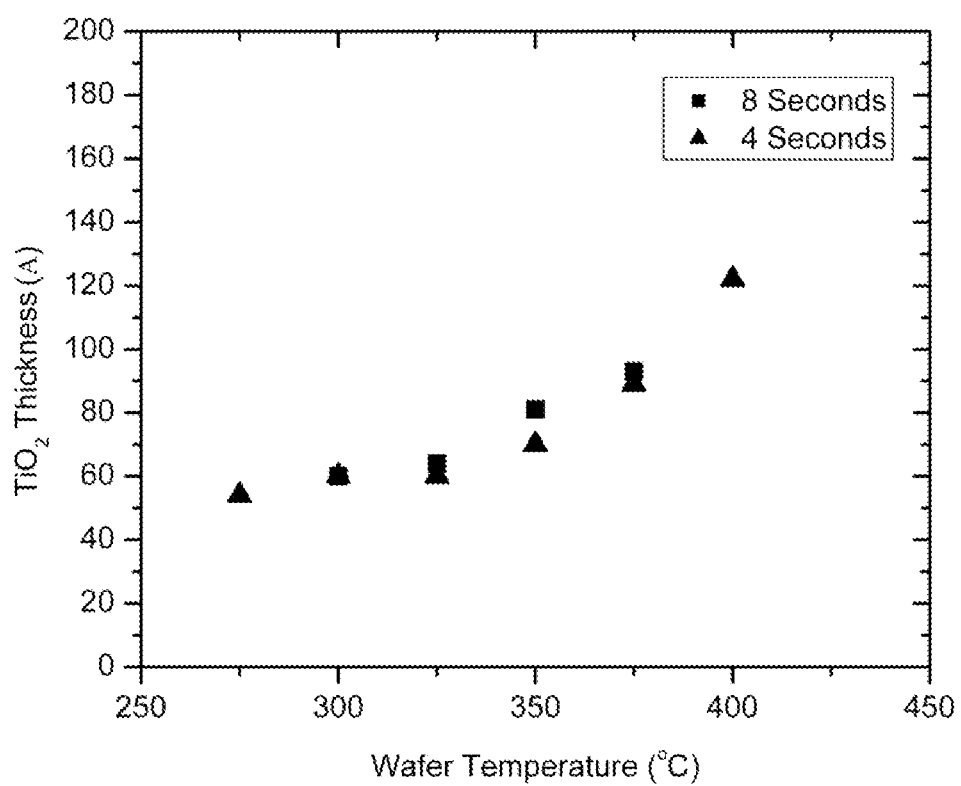
FIG. 5 is the temperature dependence of the thermal ALD of titanium oxide film using 100 ALD cycles of ozone and (2,5-di-tert-butylpyrrolyl)(tris(ethoxy)titanium, indicating that ALD thermal window for this precursor is at least up to ~330° C.

The typical ALD conditions are: Ti precursor pulse time was 4 or 8 seconds, the Ar purge time after Ti precursor pulse was 10 or 15 seconds, the ozone pulse time was 5 seconds, and the Ar purge time after ozone pulse was 10 seconds. The cycle was repeated 100 times. TiO$_2$ films were obtained and the dependence of titanium oxide thickness on deposition temperature is shown in FIG. 5. The results suggest that ALD thermal process window can be up to ~330° C. with ALD growth rate of ~0.6 A/cycle which is much higher than what disclosed in prior art for solid precursors with similar ligand system (Black, K., A. C. Jones, J. Bacsa, P. R. Chalker, P. A. Marshall, H. O. Davies, P. N. Heys, P. O'Brien, M. Afzaal, J. Raftery and G. W. Critchlow, "Investigation of new 2,5-dimethylpyrrolyl titanium alkylamide and alkoxide complexes as precursors for the liquid injection mocvd of $TiO_2$" Chemical Vapor Deposition 16(1-3): 93-99 (2010)).

The invention claimed is:

1. A liquid titanium precursor comprising (2,5-di-tert-amylpyrrolyl)(tris(ethoxy))titanium.

2. A Group 4 precursor is represented by the formula:

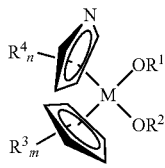

wherein M is a Group 4 metal; wherein $R^{1-2}$ are the same or different and selected from group consisting of linear or branched $C_{1-6}$ alkyls; $R^3$ are the same or different selected from the group consisting of $C_{1-6}$ alkyls, $C_{3-10}$ alkyls containing oxygen or nitrogen atoms, —$CH_2CH_2OMe$ and —$CH_2CH_2NMe_2$; m=0, 1, 2, 3, 4, 5; $R^4$ is the same or different organic groups substituted at 2, 3, 4, 5-positions of the pyrrole ring and selected from the group consisting of $C_{1-6}$ alkyls, branched $C_{3-6}$ alkyls substituted at 2, 5 positions, $C_{3-10}$ alkyls containing oxygen or nitrogen atoms, —$CH_2CH_2OMe$ and —$CH_2CH_2NMe_2$; n=1, 2, 3, 4; m=0, 1, 2, 3, 4, 5; $R^3$ and $R^4$ can be linked together.

3. The precursor of claim 2 wherein the Group 4 metal is selected from the group consisting of titanium, zirconium and hafnium.

4. The precursor of claim 3 wherein the Group 4 metal precursor is selected from the group consisting of (cyclopentadienyl)(2,5-di-methylpyrrolyl)(bis(ethoxy)titanium, (methylcyclopentadienyl)(2,5-di-methylpyrrolyl)(bis(ethoxy)titanium, (ethylcyclopentadienyl)(2,5-di-methylpyrrolyl)(bis(ethoxy)titanium, (propylcyclopentadienyl)(2,5-di-methylpyrrolyl)(bis(ethoxy)titanium, (cyclopentadienyl)(2,5-di-methylpyrrolyl)(bis(methoxy)titanium, (methylcyclopentadienyl)(2,5-di-methylpyrrolyl)(bis(methoxy)titanium, (ethylcyclopentadienyl)(2,5-di-methylpyrrolyl)(bis(methoxy)titanium, (propylcyclopentadienyl)(2,5-di-methylpyrrolyl)(bis(methoxy)titanium, (cyclopentadienyl)(2,5-di-tert-amylpyrrolyl)(bis(ethoxy))titanium, (cyclopentadienyl)(2,5-di-tert-butylpyrrolyl)(bis(ethoxy))titanium.

5. The precursor of claim 2 wherein the Group 4 metal precursor is a liquid at room temperature.

6. The precursor of claim 2 wherein the Group 4 metal precursor is a solid with melting point less than 80° C.

7. The precursor of claim 2 wherein $R^{1-2}$ can be same or different and are selected from group consisting of linear or branched $C_{1-3}$ alkyls.

8. The precursor of claim 2 wherein $R^4$ is selected from group consisting of branched $C_{1-5}$ alkyls.

9. The precursor of claim 8 wherein $R^4$ is selected from the group consisting of methyl, ethyl, propyl, tert-butyl, tert-amyl and is substituted at the 2 and 5 positions of the pyrrole ring.

10. The precursor of claim 2 containing a solvent.

11. A method of depositing a titanium metal containing film by a method selected from the group consisting of; atomic layer deposition (ALD), chemical vapor deposition (CVD), cyclic chemical vapor deposition (CCVD), MOCVD metal organic chemical vapor deposition (MOCVD), thermal chemical vapor deposition, plasma enhanced chemical vapor deposition (PECVD), photon assisted chemical vapor deposition (PACVD), plasma-photon assisted chemical vapor deposition (PPECVD), cryogenic chemical vapor deposition, chemical assisted vapor deposition, hot-filament chemical vapor deposition and plasma enhanced cyclic ALD (PEALD); wherein a liquid titanium metal precursor is used to form the titanium metal containing film, wherein the liquid titanium metal precursor comprises (2,5-di-tert-amylpyrrolyl)(tris(ethoxy)titanium.

12. The method of claim 11 wherein the titanium metal precursor includes a solvent.

13. The method of claim 11 wherein the titanium metal containing film is exposed to a post-deposition treatment selected from the group consisting of thermal and plasma; to densify the titanium metal containing film.

14. A method of depositing a Group 4 metal containing film by a method selected from the group consisting of; atomic layer deposition (ALD), chemical vapor deposition (CVD), cyclic chemical vapor deposition (CCVD), MOCVD metal organic chemical vapor deposition (MOCVD), thermal chemical vapor deposition, plasma enhanced chemical vapor deposition (PECVD), photon assisted chemical vapor deposition (PACVD), plasma-photon assisted chemical vapor deposition (PPECVD), cryogenic chemical vapor deposition, chemical assisted vapor deposition, hot-filament chemical vapor deposition and plasma enhanced cyclic ALD (PEALD); wherein a Group 4 metal precursor is used to form the Group 4 metal containing film, comprising; a Group 4 metal precursor represented by the formula:

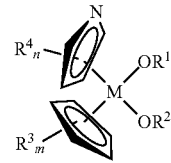

wherein M is a Group 4 metal; wherein $R^{1-2}$ are the same or different and selected from group consisting of linear or branched $C_{1-6}$ alkyls; $R^3$ are the same or different and selected from the group consisting of $C_{1-6}$ alkyls, $C_{3-10}$ alkyls containing oxygen or nitrogen atoms, —$CH_2CH_2OMe$ and —$CH_2CH_2NMe_2$; m=0, 1, 2, 3, 4, 5; $R^4$ can be same or different organic groups substituted at 2,3,4,5-positions of the pyrrole ring and selected from the group consisting of $C_{1-6}$ alkyls, branched $C_{3-5}$ alkyls substituted at 2, 5 positions, $C_{3-10}$ alkyls containing oxygen or nitrogen atoms, —$CH_2CH_2OMe$ and —$CH_2CH_2NMe_2$; n=1, 2, 3, 4; $R^3$ and $R^4$ can be linked together.

15. The method of claim 14 wherein the film is exposed to a post-deposition treatment selected from the group consisting of thermal and plasma; to densify the film.

16. The method of claim 14 wherein the Group 4 metal precursor is selected from the group consisting of (cyclopentadienyl)(2,5-di-methylpyrrolyl)(bis(ethoxy)titanium, (methylcyclopentadienyl)(2,5-di-methylpyrrolyl)(bis(ethoxy)titanium, (ethylcyclopentadienyl)(2,5-di-methylpyrrolyl)(bis(ethoxy)titanium, (propylcyclopentadienyl)(2,5-di-methylpyrrolyl)(bis(ethoxy)titanium, (cyclopentadienyl)(2,5-di-methylpyrrolyl)(bis(methoxy)titanium, (methylcyclopentadienyl)(2,5-di-methylpyrrolyl)(bis(methoxy)titanium, (ethylcyclopentadienyl)(2,5-di-methylpyrrolyl)(bis(methoxy)titanium, (propylcyclopentadienyl)(2,5-di-methylpyrrolyl)(bis(methoxy)titanium, (cyclopentadienyl)(2,5-di-tert-amylpyrrolyl)(bis(ethoxy))titanium, (cyclopentadienyl)(2,5-di-tert-butylpyrrolyl)(bis(ethoxy))titanium and mixtures thereof.

17. The method of claim 16 including a solvent selected from the group consisting of octane, ethylcyclohexane, dodecane, toluene, xylene, mesitylene, diethylbenzene, and mixture thereof.

* * * * *